United States Patent
Ye et al.

(10) Patent No.: US 6,284,513 B1
(45) Date of Patent: Sep. 4, 2001

(54) PROCESS FOR THE PRODUCTION OF STROMELYSIN CATALYTIC DOMAIN PROTEIN

(75) Inventors: Qi-Zhuang Ye; Linda Lea Johnson; Donald John Hupe; Vijaykumar Baragi, all of Ann Arbor, MI (US)

(73) Assignee: Warner-Lambert Company, Ann Arbor, MI (US)

( * ) Notice: Subject to any disclaimer, the term of this patent is extended or adjusted under 35 U.S.C. 154(b) by 0 days.

(21) Appl. No.: 08/281,313

(22) Filed: Jul. 27, 1994

Related U.S. Application Data

(63) Continuation of application No. 08/012,705, filed on Feb. 3, 1993.

(51) Int. Cl.[7] .................................................. A61L 9/01
(52) U.S. Cl. .................................. 435/226; 435/320.1
(58) Field of Search .............................. 435/226, 320.1, 435/849

(56) References Cited

PUBLICATIONS

Marcy, A.I. et al; Biochemistry 30: 6476–6483 (1991).*
Sanchez–Lopez, R. et al., J. Biol. Chem. 263: 11892–11899 (1988).*
Promega Corp. 1991/1992 Catalog, Promega Corp., Madison, WI, pp. 122, 353.*
Studier et al., Meth. Enzymol. 185: 60–89 (1990).*
Eluin et al., Gene 87: 123–126 (1990).*
Gangola et al., J. Biol. Chem. 262: 12570–12574 (1987).*
Lama et al., Gene 117: 185–192(1992).*
Chan et al., FEBS. Lett. 239: 219–222 (1988).*
McIver et al., J. Bacterial. 173:7781–7789 (1991).*
*Biochemistry*, vol. 31, No. 45, 1992: 11231–11235 Qi–Zhuang Ye, et al., Purification and Characterization of Human Stromelysin Catalytic Domain Expressed in *Escherichia coli*.
American Society for Biochemistry & Molecular Biology—83rd Biophysical Society—36th Feb. 12, 1992 Huston Texas Poster Presentation—Q–Z Ye, et al. "Cloning and Expression of Human Stromelysin Catalytic Domain in *E. coli* as a Soluble and Active Proteinase".

* cited by examiner

*Primary Examiner*—Ponnathapura Achutamurthy
*Assistant Examiner*—Kathleen Kerr
(74) *Attorney, Agent, or Firm*—Merchant & Gould P.C.

(57) ABSTRACT

A process for the production of the catalytic domain, without propeptide, of a matrix metalloproteinase is described which comprises culturing transformed host cells carrying a DNA sequence encoding the catalytic domain as well as a method for screening for inhibitors of a matrix metalloproteinase; a method for determining the 3-dimensional structure of the catalytic domain of a matrix metalloproteinase; and pharmaceutical compositions of human stromelysin catalytic domain protein which are useful in treating herniated vertebral discs, dermal ulcers, modifying scar tissue formation, and joint diseases.

9 Claims, 5 Drawing Sheets

```
Stromelysin
           10          20          30          40          50          60          70          80          90
       MKSLPILLLLCVAVCSAYPLDGAARGEDTSMNLVQKYLENYYDLEKDVKQFVRRKDSGPVVKKIREMQKFLGLEVTGKLDSDTLEVMRKPRCGVPD Stromelysin
          100         110         120         130         140         150         160         170         180         190
       VGHFRTFRGIPKWRKTHLTYRIVNYTPDLPKDAVDSAVEKALKVWEEVTPLTFSRLYEGEADIMISFAVREHGDFYPFDGPGNVLAHAYAPGPGIN
        :  :::        ::::: :: :::       :  :::: ::        ::::::  ::          ::: :::::::  ::::  :::  ::
        YSLFPNSPKWTSKVVTYRIVSYTRDLPHITVDRLVSKALNMMGKEIPLHFRKVVWGTADIMIGFARGAHGDSYPFDGPGNTLAHAFAPGTGLG
Matrilysin Stromelysin
          200         210         220         230         240         250         260         270         280
       GDAHFDDDEQWTKDTT-GTNLFLVAAHEIGHSLGLFHSANTEALMYPLYHSLTDLTRFRLSQDDINGIQSLYGPPPDSPETPLVPTEPVPPEPGTP
       ::::: ::    ::   ::  :  :::::  ::::::: :::           :  ::::::: :::   :::::
       GDAHFDEDERWTDGSSLGINFLYAATHELGHSLGMGHSSDPNAVMYPTYGN-GDPQNFKLSQDDIKGIQKLYGKRSNSRKK
Matrilysin Stromelysin
          290         300         310         320         330         340         350         360         370         380
       ANCDPALSFDAVSTLRGEILIFKDRHFWRKSLRKLEPELHLISSFWPSLPSGVDAAYEVTSKDLVFIFKGNQFWAIRGNEVRAGYPRGIHTLGFPP Stromelysin
          390         400         410         420         430         440         450         460         470
       TVRKIDAAISDKEKNKTYFFVEDKYWRFDEKRNSMEPGFPKQIAEDFPGIDSKIDAVFEEFGFFYFFTGSSQLEFDPNAKKVTHTLKSNSWLNC
```

PROCESS FOR THE PRODUCTION OF STROMELYSIN CATALYTIC DOMAIN PROTEIN

This application is a continuation of Ser. No. 08/012,705 filed Feb. 3, 1993.

BACKGROUND OF THE INVENTION

The present invention relates to a process for the production of a mammalian stromelysin catalytic domain protein, to a purified mammalian stromelysin catalytic domain protein, to pharmaceutical compositions which include the mammalian stromelysin catalytic domain protein and a pharmaceutically acceptable carrier, and to pharmaceutical methods of treatment.

Matrix metalloproteinases, such as stromelysins, collagenases, and gelatinases, are believed to be involved in connective tissue degradation (Woessner J F, *FASEB J.* 1991;5:2145–2154) in several physiological and pathological processes including the cartilage degradation in arthritis and tumor progression and metastasis (McDonnell S, Matrisian L, *Cancer Metastasis Rev.* 1990;9:305–319). Therefore, there is great interest in understanding the catalytic mechanism of these matrix metalloproteinases and designing specific inhibitors to control their activity.

Similar to other matrix metalloproteinases, the human fibroblast stromelysin (Whitham S E, Murphy G, Angel P, et al, *Biochem. J.* 1986;240:913–916; Saus J, Quinones S, Otani Y, et al, *J. Biol. Chem.* 1988;263:6742–6745) has a signal peptide for secretion, a propeptide with a cysteine residue for maintaining latency (Van Wart H E, Birkedal-Hansen H, *Proc. Natl. Acad. Sci. U.S.A.* 1990;87:5578–5582; Park A J, Matrisian L M, Kells A F, et al, *J. Biol. Chem.* 1991;266:1584–1590), a catalytic domain with a conserved sequence highly homologous with the zinc binding site in the bacterial zinc proteinase thermolysin (Vallee B L, Auld D S, *Biochemistry* 1990;29:5647–5659), and a C-terminal fragment which may be involved in substrate and inhibitor binding (Allan J A, Hembry R M, Angal S, et al, *J. Cell Sci.* 1991;99:789–795; Murphy G, Allan J A, Willenbrock F, et al, *J. Biol. Chem.* 1992;267:9612–9618). The matrix metalloproteinases are all secreted as proenzymes and are activated in vivo by a mechanism not yet determined. However, these enzymes can be activated in vitro with organomercurials, proteolytic enzymes, chaotropic agents, or heat (Okada Y, Harris E D, Nagase H, *Biochem. J.* 1988;254:731–741; Nagase H, Enghild J J, Suzuki K, Salvesen G, *Biochemistry* 1990;29:5783–5789; Koklitis P A, Murphy G, Sutton C, Angal S, *Biochem. J.* 1991;276:217–221). Removal of the propeptide from prostromelysin by proteinases and organomercurial compounds is a stepwise process (Okada, supra, 1988; Nagase, supra, 1990) which generates intermediate forms before the propeptide is removed completely by activated stromelysin. The activated enzyme undergoes autolytic cleavage at sites close to the C-terminus, producing a 28-kDa fragment as well as smaller species (Okada, supra, 1988; Koklitis, supra, 1991). The instability of matrix metalloproteinases due to the autodegradation may partially account for the difficulty in structural determination by X-ray crystallography. Matrilysin (formerly called PUMP) is a unique member of this enzyme family in that it lacks the C-terminal portion found in stromelysins, collagenases, and gelatinases (Muller D, Quantin B, Gesnel M-C, et al, *Biochem. J.* 1988;253:187–192). C-Terminal-deleted stromelysin and collagenase have been made and they have shown activity similar to the full-length enzymes (Marcy A I, Eiberger L L, Harrison R, et al, *Biochemistry* 1991;30:6476–6483; Lowry C L, McGeehan G, LeVine H I, *Proteins: Struct., Funct., Genet.* 1992;12:42–48; Murphy, supra, 1992). Thus, Marcy, supra, 1991, expressed a truncated stromelysin containing the catalytic domain and the propeptide. The propeptide was removed in vitro to generate the catalytic domain (Marcy, supra, 1991; Salowe S P, Marcy A I, Cuca G C, et al, *Biochemistry* 1992;31:4535–4540). Lowry, supra, 1992, described a stability study using a recombinant 19-kDa collagenase catalytic domain. However, the expression and purification of the collagenase catalytic domain have not been described. More recently, Murphy, supra, 1992, expressed the C-terminal-deleted procollagenase and prostromelysin in mouse cells. Therefore, the N-terminal catalytic domain of stromelysin is responsible and sufficient for the proteinase activity, and the C-terminal portion can be removed without major modification to the active site of the catalytic domain.

As mentioned above, matrix metalloproteinases share high sequence homology. Catalytic domains in each of the metalloproteinases can be identified by sequence comparison as described in the literature (Murphy G J P, et al, *FEBS* 1991;289:4–7; Muller, supra, 1988; Woessner, supra, 1991).

The object of the present invention is the expression, purification, and characterization of a 20-kDa stromelysin catalytic domain (SCD) protein lacking both the propeptide and the C-terminal fragment (FIG. 1). The removal of the propeptide eliminates the need for proteolytic or chemical activation, and the removal of the C-terminal fragment removes autolytic sites, thereby making the protein resistant to autodegradation. The active and stable protein with a mass of 20-kDa is suitable for structure determination by nuclear magnetic resonance spectroscopy and X-ray crystallography, as well as mechanistic studies of catalysis and inhibition. Additionally, the protein is useful in the therapy of various disease states.

SUMMARY OF THE INVENTION

Accordingly, the present invention is directed to a process for the production of the catalytic domain, without propeptide, of a matrix metalloproteinase, comprising culturing transformed host cells carrying a DNA sequence encoding the catalytic domain wherein the host cells are selected from the group consisting of bacterial cells, yeast cells, insect cells, and mammalian cells.

In a preferred embodiment of the first aspect of the invention, an *Escherichia coli* host cell transformed with a replicable expression vector under the control of a promotor such as, for example, a bacterial phage T7 promoter, or a non T7 promoter, such as, for example, T3, sp6, Tac, Trc, Trp, lac, λPL, and λPR, and the like, expresses a recombinant catalytic domain protein.

In a more preferred embodiment of the first aspect of the invention, the *Escherichia coli* host cell comprises *Escherichia coli* strains having F pili.

In a most preferred embodiment of the first aspect of the invention, the *Escherichia coli* strain having F pili is DH5αF'IQ; the expression vector is pGEMEX-D; the catalytic domain protein is human stromelysin catalytic domain protein having the sequence specified in FIG. 1; and the expression of human stromelysin catalytic domain protein is under the control of bacterial phage T7 promoters.

In a second aspect, the present invention consists of a plasmid pGEMEX-D capable of expressing stromelysin catalytic domain protein which is constructed by inserting a cDNA fragment encoding for the protein into plasmid pGEMEX-1.

In a third aspect, the present invention consists of a purified human stromelysin catalytic domain protein having the sequence specified in FIG. 1.

In a fourth aspect, the present invention consists of a method for determining the ability of a candidate substance to inhibit a matrix metalloproteinase comprising the steps of:

(a) obtaining a matrix metalloproteinase catalytic domain protein;

(b) admixing a candidate substance with the protein; and (c) determining the ability of the protein to cleave a substrate in the presence of the candidate substance.

In a preferred embodiment of the fourth aspect of the invention, the matrix metalloproteinase catalytic domain protein is human stromelysin catalytic domain protein and the substrate is selected from the group consisting of proteoglycan and thiopeptolide.

In a fifth aspect, the present invention consists of a method for determining the 3-dimensional structure of the catalytic domain of a matrix metalloproteinase by X-ray crystallography.

In a preferred embodiment of the fifth aspect of the invention, the matrix metalloproteinase is selected from the group consisting of stromelysins, collagenases, gelatinases, and matrilysin.

In a more preferred embodiment of the fifth aspect of the invention, the metalloproteinase is human stromelysin.

In a sixth aspect, the present invention consists of a method for structural determination by nuclear magnetic resonance spectroscopy of a matrix metalloproteinase using isotope labelled human stromelysin catalytic domain protein wherein the label is $^{15}N, ^{13}C$ and $^2H$.

As an active stable protein, the stromelysin catalytic domain protein will be useful in the treatment of various diseases. International Published Application WO 87/07907 discloses that mammalian stromelysin or prostromelysin is used in the debridement of dermal ulcers, modification of scar tissue formation arising from the healing of wounds such as burns and necrosis, and in the treatment of herniated vertebral discs.

Thus, in a seventh aspect, the present invention consists of a method of treating herniated vertebral discs comprising administering to a mammal suffering therefrom a therapeutically effective amount of the human stromelysin catalytic domain protein in unit dosage form.

In an eighth aspect, the present invention consists of a method of treating dermal ulcers comprising administering to a mammal suffering therefrom a therapeutically effective amount of the human stromelysin catalytic domain protein in unit dosage form.

In a ninth aspect, the present invention consists of a method of modifying scar tissue formation comprising administering to a mammal suffering therefrom a therapeutically effective amount of the human stromelysin catalytic domain protein in unit dosage form.

In a tenth aspect, the present invention consists of a method of treating joint diseases amenable to treatment comprising administering to a mammal suffering therefrom a therapeutically effective amount of the human stromelysin catalytic domain protein in unit dosage form.

In the eleventh aspect, the present invention consists of a pharmaceutical composition adapted for administering a therapeutically effective amount of the human stromelysin catalytic domain protein in admixture with a pharmaceutically acceptable excipient, diluent, or carrier in the treatment methods mentioned above.

In the twelfth aspect, the present invention consists of a method of using the human stromelysin catalytic domain protein to hydrolyze a protein substrate.

BRIEF DESCRIPTION OF THE DRAWINGS

The invention is further described by the following non-limiting examples which refer to the accompanying diagrams, FIGS. 1 to 5 and Tables 1 to 2, short particulars of which are given below.

FIG. 1 shows a comparison of the amino acid sequences of prostromelysin (SEQ ID NO:1) and the mature matrilysin (SEQ ID NO:2). The identical amino acids in both prostromelysin and matrilysin are marked by colons. The signal peptide is double underlined and the propeptide is in italics. The sequence for SCD protein is underlined.

DETAILED DESCRIPTION OF THE INVENTION

Expression of the SCD Protein

Figure 2:
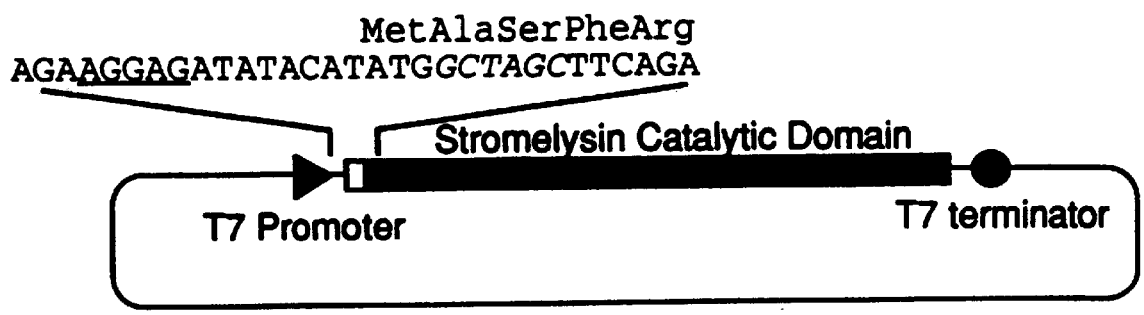
FIG. 2 shows the structure of the plasmid pGEMEX-D (3.7 kb) for expressing SCD protein. Shown in detail is the sequence (DNA SEQ ID NO:3; amino acid SEQ ID NO:4) surrounding the N-terminus of the gene, where the ribosome binding site is underlined and the Nhe1 site is in italics. Three amino acid residues (Met, Ala, and Ser) were added to the N-terminus of SCD protein as shown.

An efficient expression vector was constructed using T7 RNA polymerase (Tabor S, Richardson C C, *Proc. Natl. Acad. Sci. U.S.A.* 1985;82:1074–1078; Studier F W, Rosenberg A H, Dunn J J, Dubendorff J W, *Methods Enzymol.* 1990;185:60–89) for producing large quantities of SCD protein (FIG. 2). The SCD protein gene was fused in-frame to the 5' region of T7 phage gene 10 and replaced most of the gene 10 sequence originally on pGEMEX-1. The recombinant plasmid PGEMEX-D was introduced into DH5αF'IQ, and the SCD protein expression was initiated by introduction of a M13 phage carrying the T7 RNA polymerase gene.

The expression of the SCD protein under the control of T7 RNA polymerase was efficient. Most SCD protein was generated as insoluble protein when the expression was carried out at 37° C. By lowering the incubation temperature to 27° C., a considerable amount of soluble SCD protein was obtained. Further lowering of the temperature resulted in a much slower growth rate without increasing the SCD protein yield. Although the SCD protein was expressed as an active proteinase without propeptide, no significant effect on cell growth was observed during expression of the SCD protein either as a soluble or as an insoluble protein.

Purification of the SCD Protein

Figure 3:
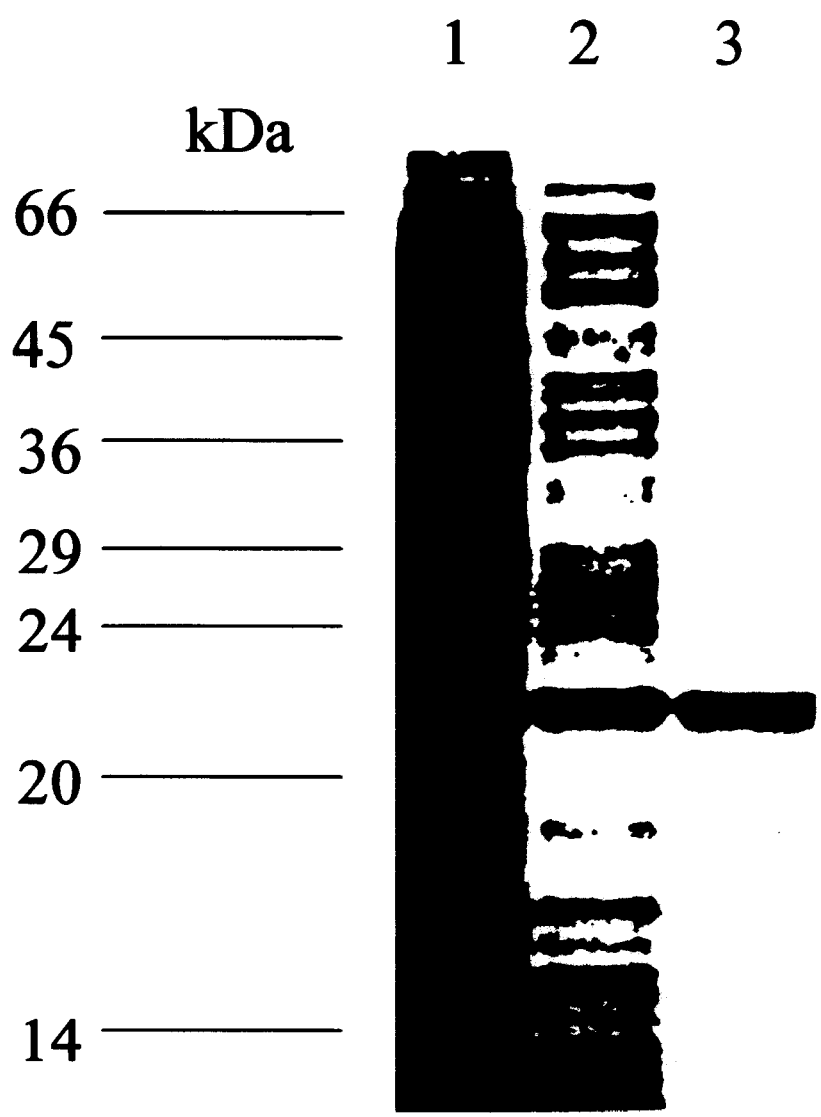
FIG. 3 shows the purification of the soluble SCD protein as analyzed by SDS-polyacrylamide gel electrophoresis and Coomassie blue staining. Lane 1, whole cell extract. Lane 2, after phenyl-Sepharose column. Lane 3, after Q-Sepharose column.

The cells grown at 27° C. were used for purifying soluble SCD protein. The SCD protein bound tightly to phenyl-Sepharose in the presence of 1 M ammonium sulfate and was eluted from the column with a decreasing gradient of ammonium sulfate. The binding of SCD protein to Q-Sepharose was weak so that it is necessary to adjust the conductivity of the SCD protein solution to <10 mS. The protein solution was loaded onto the Q-Sepharose column, and the protein was eluted with a shallow gradient of NaCl (0–200 mM). The protein purified through the two columns appeared to be homogeneous on SDS-polyacrylamide gel (FIG. 3, Table 1).

In order to maximize the yield of SCD protein, the cells were grown at 37° C. for 6 hours after induction. Under those conditions, almost all of the SCD protein was present in the insoluble portion after centrifugation of the lysed cells. This step enriched the SCD protein in the pellet as the major protein component. The pellet was solubilized in 8 M guanidine hydrochloride. Upon dilution, the SCD protein refolded quickly to the active form in the presence of $Ca^{2+}$ and $Zn^{2+}$ ions. The high recovery of protein and high specific activity after refolding (Table 1) indicated that the refolding was efficient. The refolded SCD protein was purified to apparent homogeneity the same way as for soluble SCD protein (Table 1). Similar specific activities were obtained for the SCD protein purified from either soluble or insoluble protein, indicating that the SCD protein was correctly refolded.

Sequence of the SCD Protein

The DNA sequence for the SCD protein gene in pGEMEX-D was confirmed by DNA sequencing and it predicted that the expressed SCD protein would contain three extra amino acids (Met, Ala, and Ser) at the N-terminus. However, the amino acid sequencing for the purified SCD protein showed the N-terminal sequence as FRTFPGIPKWRKTHLTYRIVNYTPDLPKDAVDSAVEK. SEQ ID No: 5 The purified SCD protein had the same N-terminus as that found in authentic stromelysin with the extra three amino acid residues (Met, Ala, and Ser) removed. This result is consistent with reports that stromelysin has the ability to process intermediates during activation (Okada, supra, 1988; Nagase, supra, 1990). The molecular weight of the purified SCD protein was determined by electrospray mass spectrometry. The determined molecular weight of 19494.1 (±0.1%) was consistent with a SCD protein starting with Phe-100 and ending with Pro-273 (predicted molecular weight 19494.1).

Hydrolysis of Thiopeptolide by the SCD Protein

Figure 4:
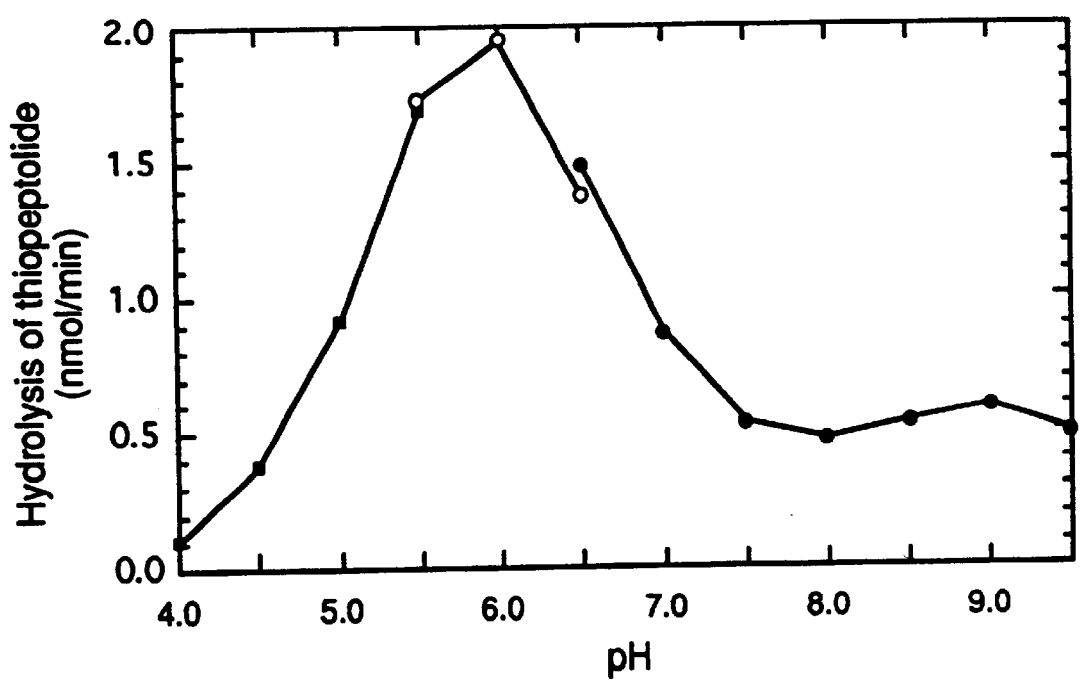
FIG. 4 shows the hydrolysis of the thiopeptolide substrate at different pHs. The activity of the purified SCD protein was determined as described under Materials and Methods in 100 mM acetate (closed squares), MES (open circles), and Bis-Tris propane (closed circles) at the pHs indicated.

The SCD protein showed high activity in hydrolyzing the thiopeptolide substrate developed for vertebrate collagenase (Weingarten H, Feder J, Anal. Biochem. 1985;147:437–440). Under our assay conditions, the thiopeptolide showed no detectable decomposition without enzyme unless the pH was increased to above 8.0. The SCD protein showed activity at neutral pH but had the highest activity at pH 6.0, more than twice the activity of pH 7.0 (FIG. 4). This pH-activity curve is similar to those found for full-length stromelysin (Galloway W A, Murphy G, Sandy J D, et al, Biochem. J. 1983;209:741–752; Gunja-Smith Z, Nagase H, Woessner J F, Biochem. J. 1989;258:115–119). At pH 6.0, the SCD protein has a $K_m$ of 270 $\mu$M and a $k_{cat}$ of 127 $min^{-1}$.

Hydrolysis of Proteoglycan by the SCD Protein

The SCD protein cleaves the natural substrate proteoglycan as assayed by the proteoglycan-polyacrylamide particle assay (Nagase H, Woessner J F, Anal. Biochem. 1980;107:385–392; Baragi V M, Jordan H, Renkiewicz R, J. Pharmacol. Toxicol. Methods 1992;27:101–105). The cleavage was inhibited by chelators such as EDTA and 1,10-phenanthroline (Table 2). However, inhibitors of serine (PMSF), cysteine (N-ethylmaleimide, leupeptin), or aspartyl (pepstatin) proteinases did not significantly inhibit the enzyme. Also, phosphoramidon, a thermolysin inhibitor with no inhibitory effect on matrix metalloproteinases, did not inhibit the enzyme. Furthermore, U24522, a synthetic inhibitor known to inhibit proteoglycan-degrading metalloproteinases (Caputo C B, Wolanin D J, Roberts R A, et al, Biochem. Pharmacol. 1987;36:995–1002), effectively inhibited SCD protein. On the basis of these data, the activity measured using the proteoglycan substrate is consistent with the activity of proteoglycan-degrading matrix metalloproteinases.

Stability of the SCD Protein

Figure 5A:
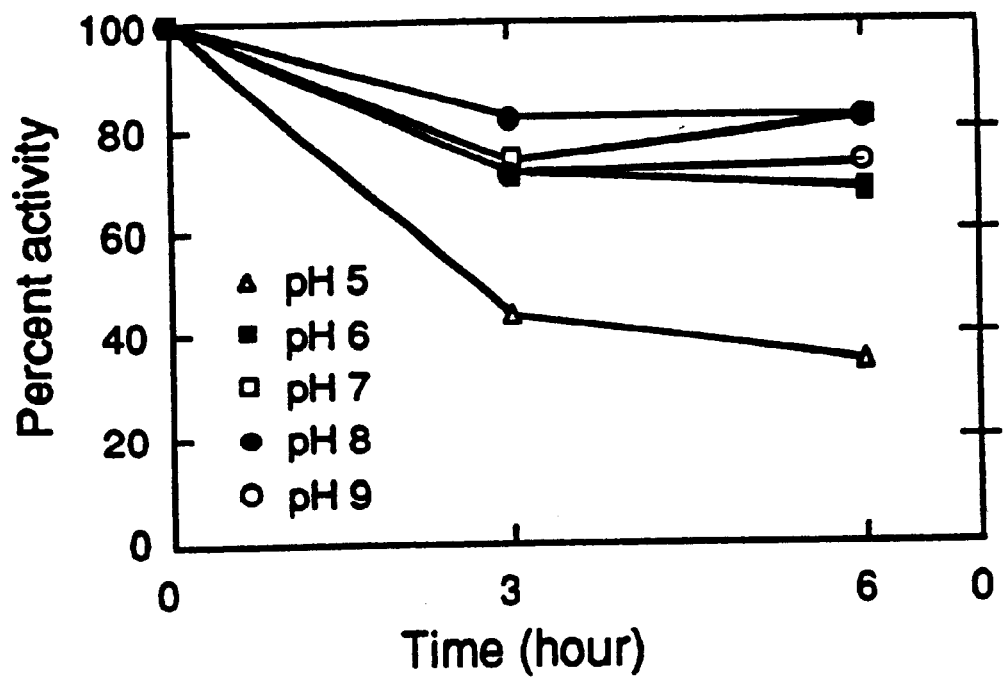
FIGS. 5A and 5B show the thermal stability of SCD protein in the presence of $CaCl_2$. The SCD protein was incubated at 37° C. at the pHs indicated in the presence of 10 (A) or 0.5 mM (B) $CaCl_2$ and aliquots were taken after the time intervals. Activity was assayed as the thiopeptolide hydrolysis at pH 6.0.
Figure 5B:
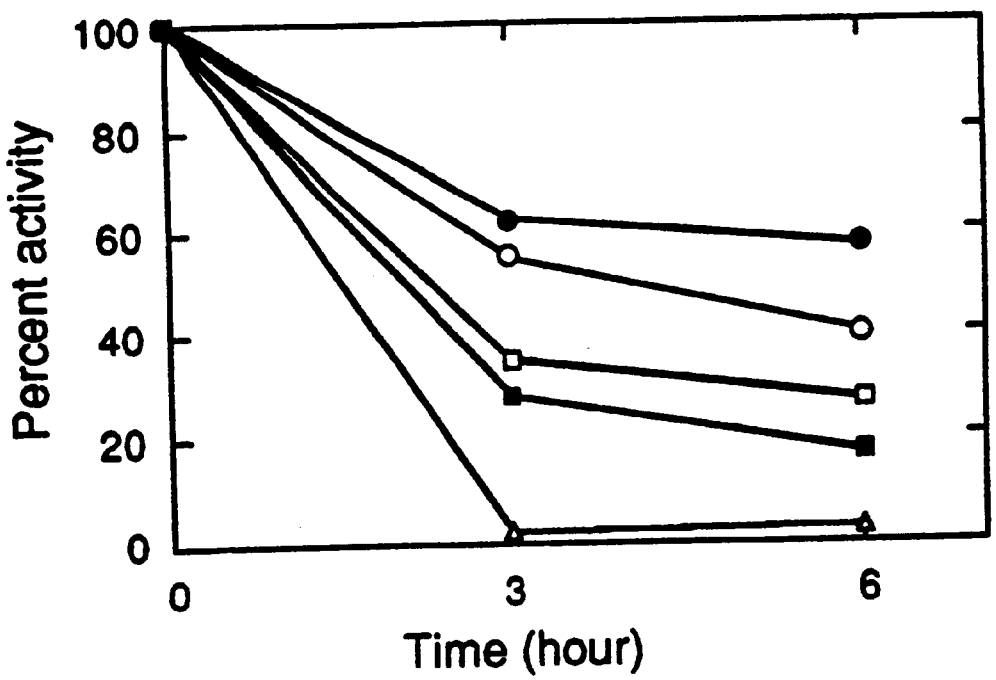

The purified SCD protein is stable in 50 mM Tris.HCl (pH 7.6) and 10 mM $CaCl_2$ at 4° C. At 37° C., it was stable at pH 6–9 in the presence of 10 mM $CaCl_2$, and it showed a significant decrease in activity when the pH was dropped to 5.0 in acetate buffer (FIG. 5A). However, at the lower $CaCl_2$ concentration (0.5 mM), the activity decreased over a 6-hour period, most quickly at pH 5.0 (FIG. 5B). In another experiment, SCD protein retained considerable amounts of activity at pH 6.0, 7.0, or 8.0 with 10 mM $CaCl_2$ (43%, 69%, and 83%, respectively) after incubation at 37° C. for 24 days. SDS-PAGE analysis showed that the activity correlated with the protein band at 20 kDa and that the loss of activity accompanied the appearance of lower molecular weight proteins. The $Ca^{2+}$ ion appeared to stabilize the SCD protein as found by Lowry, supra, 1992, from a similar collagenase fragment.

TABLE 1

Purification of SCD Protein

| | Vol (mL) | Protein Conc (mg/mL) | Protein (mg) | Act[a] (units) | Recovery (%) | Sp Act. (units/mg) | Purification (x-fold) |
|---|---|---|---|---|---|---|---|
| Soluble Protein[b] | | | | | | | |
| Cell extract | 34.7 | 9.7 | 337 | 6.33 | 100 | 0.019 | 1 |
| Phenyl-Sepharose | 31.0 | 1.4 | 43.4 | 12.02 | 190 | 0.277 | 15 |
| Q-Sepharose | 1.25 | 0.88 | 1.1 | 5.19 | 82 | 4.72 | 248 |
| Insoluble Protein[c] | | | | | | | |
| 8 M Guanidine hydrochloride | 11.5 | 13.6 | 156 | | | | |
| Refolding | 300 | 0.16 | 48 | 110 | 100 | 2.29 | 1 |

TABLE 1-continued

Purification of SCD Protein

|  | Vol (mL) | Protein Conc (mg/mL) | Protein (mg) | Act[a] (units) | Recovery (%) | Sp Act. (units/mg) | Purification (x-fold) |
| --- | --- | --- | --- | --- | --- | --- | --- |
| Phenyl-Sepharose | 5.2 | 4.9 | 25 | 93.6 | 85 | 3.74 | 1.6 |
| q-Sepharose | 5.0 | 3.8 | 19 | 76.7 | 70 | 4.04 | 1.8 |

[a]The activity was followed by a thiopeptolide assay as described under Materials and Methods. A unit of activity is defined as micromoles of product per minute at room temperature (22° C.).
[b]From a 2-L culture, 6.34 g of cell paste.
[c]From a 1-L culture, 5.97 g of cell paste.

TABLE 2

Inhibition of Proteoglycan-Degrading SCD Protein

| Inhibitor | Conc | Proteoglycan Degradation (µg of Chondroitin Sulfate/h) | Percent Inhibition[a] |
| --- | --- | --- | --- |
| No Inhibitor |  | 8.0 | 0 |
| EDTA | 5 mM | 0.7 | 91 |
| 1,10-Phenanthroline | 4 mM | 0.0 | 100 |
| PMSF | 500 µM | 7.4 | 7 |
| N-Ethylmaleimide | 10 mM | 6.9 | 30 |
| Leupeptin | 10 µg/mL | 5.6 | 14 |
| Pepstatin | 1 µg/mL | 7.2 | 10 |
| Phosphoramidon | 25 µM | 8.2 | 0 |
| U24522 | 5 µM | 0.8 | 90 |

[a]Ratio of proteoglycan degradation in the presence and absence of inhibitors

The SCD protein of the present invention is stable and fully active as a proteinase and it is useful in mechanistic studies on catalysis and inhibition. Furthermore, the present invention discloses an efficient expression system and simple purification scheme for SCD protein. Additionally, the recombinant SCD protein can be obtained in large quantities.

Thus, SCD protein can be used to determine the 3-dimensional structure of the catalytic domain of a matrix metalloproteinase by X-ray crystallography or nuclear magnetic resonance spectroscopy, which is carried out by methodology known in the art.

Also, SCD protein can be used in a screening assay to uncover inhibitors of a matrix metalloproteinase which comprises mixing SCD protein with the candidate compound and determining the ability of SCD protein to cleave a substrate. Substrates such as, for example, proteoglycan, thiopeptolide, and the like may be used in the assay.

Additionally, SCD protein may be used to hydrolyze a protein substrate by methodology known in the art.

The protein of the present invention can be prepared and administered in a wide variety of oral and parenteral dosage forms. Thus, the protein of the present invention can be administered by injection, that is, intravenously, intramuscularly, intracutaneously, subcutaneously, intraduodenally, or intraperitoneally. Also, the protein of the present invention can be administered by inhalation, for example, intranasally. Additionally, the protein of the present invention can be administered transdermally. It will be obvious to those skilled in the art that the following dosage forms may comprise as the active component, either the protein or a corresponding pharmaceutically acceptable salt of the protein.

For preparing pharmaceutical compositions from the protein of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as an agent for treating herniated vertebral discs, dermal ulcers, modifying scar tissue formation, or joint diseases, the protein utilized in the pharmaceutical method of this invention are administered at the initial dosage of about 0.01 mg to about 20 mg per kilogram daily. A daily dose range of about 0.01 mg to about 10 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the protein. Thereafter, the dosage is increased by small increments until the optimum effect under the circumstances is reached. For convenience, the total daily dosage may be divided and administered in portions during the day, if desired.

The following nonlimiting examples illustrate the inventor's preferred methods for preparing the protein of the invention.

Materials and Methods

Materials

Figure 6:
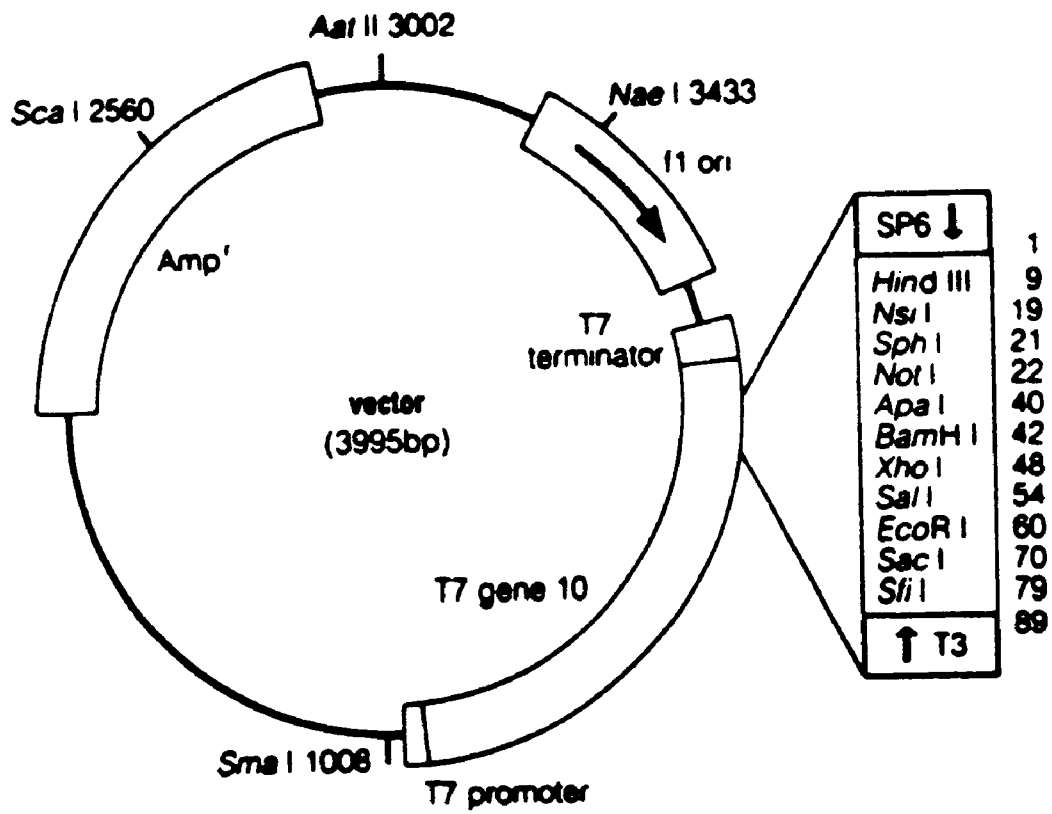
FIG. 6 shows the vector map for pGEMEX-1.

Oligonucleotide primers for PCR were synthesized on a Model 392 DNA synthesizer (Applied Biosystems, Foster City, Calif.) and were purified with oligonucleotide purification cartridge (OPC cartridge) (Applied Biosystems). The sequence for the forward primer F was GGATCAC-CAGCTAGC_TATCCATTGGATGGAGCTGCA_, Seq ID NO: 6 and that for the reverse primer R was GCACTC-GAATTCTGCAGTCA _GGGGGTCTCAGGGGAGTCAG_, Seq ID NO: 7 where the sequences from the stromelysin gene are underlined and the restriction sites Nhe1 and EcoR1 are in italics. The cDNA fragment containing the stromelysin gene (Whitham, supra, 1986; Saus, supra, 1988) was provided by Dr. C. E. Brinkerhoff (Dartmouth). The *Escherichia coli* strain DH5αF'IQ was purchased from BRL (Gaithersburg, Md.). The plasmid vector pGEMEX-1 as dipicted in FIG. 6 was obtained from Promega (Madison, Wis.) and the M13 phage carrying T7 RNA polymerase (M13/T7) was from Invitrogen (San Diego, Calif.). Restriction and ligation enzymes, as well as Vent DNA polymerase, were from New England Biolabs (Beverly, Mass.). The thiopeptolide Ac-Pro-Leu-Gly-thioester-Leu-Leu-Gly-OEt Seq ID No: 8 was obtained from Bachem Bioscience (Philadelphia, Pa.). Inhibitor U24522 (Caputo, supra, 1987) was synthesized by literature procedures. Protease inhibitors leupeptin, aprotinin, and pepstatin were from Boehringer Mannheim (Indianapolis, Ind.). Phenyl-Sepharose and Q-Sepharose were purchased from Pharmacia LKB (Piscataway, N.J.).

EXAMPLE 1

Preparation of SCD Protein

Step 1. Construction of the Expression Vector pGEMEX-D

Human cDNA containing the stromelysin gene (Whitham, supra, 1986; Saus, supra, 1988) was amplified by PCR with the primers F and R to obtain the gene fragment coding for amino acid residues 100 through 273 (FIG. 1). The primers were designed to introduce Nhe1 restriction site at the beginning of the gene and EcoR1 site at the end. The PCR fragment was digested with Nhe1 and EcoR1 and ligated with plasmid vector pGEMEX-1, which was previously digested with Nhe1 and EcoR1 and dephosphorylated with calf intestine alkaline phosphatase. The recombinant plasmid pGEMEX-D (FIG. 2) was transformed into *Escherichia coli* strain DH5αF'IQ. The plasmid was analyzed by restriction digestion and the DNA sequence for the SCD protein gene was confirmed by the dideoxy sequencing method.

Step 2—Expression of the SCD Protein

Two liters of 2×TY medium (16 g tryptone, 10 g yeast extract, 5 g NaCl per liter) containing ampicillin (50 $\mu$g/mL) and kanamycin (30 $\mu$g/mL) were inoculated with 20 mL of overnight culture of DH5αF'IQ/pGEMEX-D in the same medium. Cells were cultured at 37° C. to an $OD_{600}$ of about 0.8 before induction by adding the phage M13/T7 (plaque forming unit per mL=1×10$^{11}$, multiplicity of infection=10), and isopropyl-1-thio-β-D-galactoside (IPTG) (1 mM final concentration). In order to maximize the production of soluble SCD protein, the temperature was lowered to 27° C. after induction and the incubation was continued at 27° C. for 4 hours before harvesting by centrifugation. In order to maximize the production of insoluble SCD protein, the incubation at 37° C. was continued for 6 hours after induction. The cells were frozen immediately and kept at −20° C. until use.

Step 3—Purification of Soluble SCD Protein

Cells (6.34 g wet weight) grown at 27° C. were resuspended in 25 mL of 100 mM Tris.HCl (pH 7.6) buffer containing 5 mM $CaCl_2$, 0.5 mM $ZnCl_2$ and the protease inhibitors leupeptin, aprotinin, and pepstatin (1 $\mu$g/mL each). The suspension was passed through a French press twice at 14,000 psi and the lysate was centrifuged at 20,000 g for 30 minutes at 4° C. Ammonium sulfate was added to the supernatant to 20% saturation, and the mixture (30 mL) was centrifuged, loaded onto a phenyl-Sepharose column (180 mL) previously equilibrated with 50 mM Tris.HCl (pH 7.6), 5 mM $CaCl_2$, 1 M $(NH_4)_2SO_4$, and eluted with a linear gradient of decreasing $(NH_4)_2SO_4$ (1 M to 0 M) and increasing $CaCl_2$ (5 mM to 20 mM) in 50 mM Tris.HCl (pH 7.6). The active fractions were combined and concentrated to a 10-mL volume through a YM10 membrane in an Amicon stirred cell (Amicon, Beverly, Mass.). The conductivity was adjusted during the concentration with 50 mM Tris.HCl (pH 7.6), 10 mM $CaCl_2$ to about 8 mS ($m\Omega^{-1}$/cm). The protein solution (10 mL) was loaded onto a Q-Sepharose column (180 mL) previously equilibrated with 50 mM Tris.HCl (pH 7.6), 10 mM $CaCl_2$, and the protein was eluted from the column with the same buffer containing 200 mM NaCl with a linear gradient (0–100%). The purified SCD protein was concentrated and stored in 50 mM Tris.HCl (pH 7.6), 10 mM $CaCl_2$ at 4° C.

Step 4—Refolding and Purification of Insoluble SCD Protein

The cells (5.97 g wet weight) grown at 37° C. were resuspended in 25 mL of 50 mM Tris.HCl buffer (pH 7.6) and lysed by two passages through a French press at 14,000 psi. The pellet obtained after centrifugation (20,000 g, 30 minutes) was washed twice with 50 mM Tris.HCl and solubilized with 10 mL of 8 M guanidine hydrochloride. The mixture was centrifuged at 20,000 g for 20 minutes. The supernatant was added dropwise to a 100-mL refolding buffer (stirred at 4° C.) containing 50 mM Tris.HCl (pH 7.6), 10 mM CaCl$_2$, 0.1 mM ZnCl$_2$, and the protease inhibitors leupeptin, aprotinin, and pepstatin (1 μg/mL each). The refolding mixture was centrifuged at 20,000 g for 20 minutes. The pellets were dissolved in another 10 mL of 8 M guanidine hydrochloride and the refolding was repeated twice. The supernatants from the three refoldings were combined and ammonium sulfate was added to 20% saturation. The solution containing the SCD protein was purified on phenyl-Sepharose and Q-Sepharose columns as described for soluble SCD protein.

EXAMPLE 2
Thiopeptolide Assay

The hydrolysis of the thiopeptolide Ac-Pro-Leu-Gly-thioester-Leu-Leu-Gly-OEt, Seq ID NO: 8 originally developed for vertebrate collagenase (Weingarten, supra, 1985), was used to follow the SCD protein activity. A 100 μL assay mixture contained 50 mM MES (pH 6.0), 10 mM CaCl$_2$, 100 μM thiopeptolide substrate, and 1 mM DTNB. The substrate concentration was varied from 10 μM to 800 μM to obtain $K_m$ and $k_{cat}$. The change of absorbance at 405 nm was monitored on a ThermoMax microplate reader (Molecular Devices, Menlo Park, Calif.) at room temperature (22° C.). The calculation was based on the $\epsilon_{412}=13{,}600$ M$^{-1}$ cm$^{-1}$ for the DTNB-derived product 3-carboxy-4-nitrothiophenoxide (Ellman GL, *Arch, Biochem. Biophys.* 1959;82:70–77),

EXAMPLE 3
Proteoglycan Degradation Assay

The proteinase activity was measured using the proteoglycan-polyacrylamide particle assay (Nagase, supra, 1980) that was modified for screening enzyme inhibitors (Baragi, supra, 1992). The assays were conducted in a final volume of 200 μL containing 50 mM Tris.HCl (pH 7.4), 5 mM CaCl$_2$, 200 mM NaCl, 0.02% NaN$_3$, 7 μg of SCD protein, and 4 mg of proteoglycan-polyacrylamide particles (150±20 μg of chondroitin sulfate/mg of particles). The incubations were carried out in the presence or absence of inhibitors for 16 hours at 37° C. Enzyme activity was expressed as micrograms of chondroitin sulfate released per hour.

---

What is claimed is:

1. A one step in vivo process for the production of a catalytic domain, without propeptide, of human stromelysin, consisting of culturing transformed *Escherichia coli* host cells comprising a DNA sequence encoding said catalytic domain.

2. A process according to claim 1 wherein an *Escherichia coli* host cell transformed with a replicable expression vector expresses a recombinant human stromelysin catalytic domain protein.

3. A process according to claim 2 wherein the catalytic domain protein is human stromelysin catalytic domain protein having the sequence specified for the mature stromelysin catalytic domain protein featured in Sequence ID No. 1.

4. A process according to claim 3 wherein the expression of human stromelysin catalytic domain protein is under the control of bacterial phage T7 promoter.

5. A process according to claim 2 wherein the *Escherichia coli* host cell comprises *Escherichia coli* strains having F pili.

6. A process according to claim 5 wherein the *Escherichia coli* strain having F pili is DH5αF'IQ.

7. A process according to claim 2 wherein the expression vector is pGEMEX-D.

8. A process according to claim 3 wherein the expression of human stromelysin catalytic domain protein is under the control of a non T7 promoter selected from the group consisting of a phage T3 promoter; a phage sp6 promoter; *Escherichia coli* Tac promoter; *Escherichia coli* Trc promoter; *Escherichia coli* Trp promoter; *Escherichia coli* lac promoter; a phage λP$_L$ promoter; and a phage λP$_R$ promoter.

9. A plasmid pGEMEX-D capable of expressing a human stromelysin catalytic domain protein which is constructed by inserting a cDNA fragment encoding said human stromelysin catalytic domain protein into the plasmid depicted in FIG. 6.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 477 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Protein
      (B) LOCATION: 100..273
      (D) OTHER INFORMATION: /note= "Mature stromelysin catalytic
         domain protein"

(ix) FEATURE:
      (A) NAME/KEY: Region
      (B) LOCATION: 1..17
      (D) OTHER INFORMATION: /note= "Signal peptide"

(ix) FEATURE:
      (A) NAME/KEY: Region
      (B) LOCATION: 18..99
      (D) OTHER INFORMATION: /note= "Propeptide"

(xi) SEQUENCE DESCRIPTION: SEQ ID NO:1:

```
Met Lys Ser Leu Pro Ile Leu Leu Leu Cys Val Ala Val Cys Ser
            -95                 -90                 -85

Ala Tyr Pro Leu Asp Gly Ala Ala Arg Gly Glu Asp Thr Ser Met Asn
            -80                 -75                 -70

Leu Val Gln Lys Tyr Leu Glu Asn Tyr Tyr Asp Leu Glu Lys Asp Val
        -65                 -60                 -55

Lys Gln Phe Val Arg Arg Lys Asp Ser Gly Pro Val Val Lys Lys Ile
    -50                 -45                 -40

Arg Glu Met Gln Lys Phe Leu Gly Leu Glu Val Thr Gly Lys Leu Asp
-35                 -30                 -25                 -20

Ser Asp Thr Leu Glu Val Met Arg Lys Pro Arg Cys Gly Val Pro Asp
```

```
                    -15                 -10                  -5
Val Gly His Phe Arg Thr Phe Pro Gly Ile Pro Lys Trp Arg Lys Thr
                 1               5              10

His Leu Thr Tyr Arg Ile Val Asn Tyr Thr Pro Asp Leu Pro Lys Asp
             15              20              25

Ala Val Asp Ser Ala Val Glu Lys Ala Leu Lys Val Trp Glu Glu Val
 30              35              40                          45

Thr Pro Leu Thr Phe Ser Arg Leu Tyr Glu Gly Ala Asp Ile Met
             50              55              60

Ile Ser Phe Ala Val Arg Glu His Gly Asp Phe Tyr Pro Phe Asp Gly
             65              70              75

Pro Gly Asn Val Leu Ala His Ala Tyr Ala Pro Gly Pro Gly Ile Asn
         80              85              90

Gly Asp Ala His Phe Asp Asp Asp Glu Gln Trp Thr Lys Asp Thr Thr
 95             100             105

Gly Thr Asn Leu Phe Leu Val Ala Ala His Glu Ile Gly His Ser Leu
110             115             120             125

Gly Leu Phe His Ser Ala Asn Thr Glu Ala Leu Met Tyr Pro Leu Tyr
             130             135             140

His Ser Leu Thr Asp Leu Thr Arg Phe Arg Leu Ser Gln Asp Asp Ile
             145             150             155

Asn Gly Ile Gln Ser Leu Tyr Gly Pro Pro Asp Ser Pro Glu Thr
         160             165             170

Pro Leu Val Pro Thr Glu Pro Val Pro Pro Glu Pro Gly Thr Pro Ala
             175             180             185

Asn Cys Asp Pro Ala Leu Ser Phe Asp Ala Val Ser Thr Leu Arg Gly
190             195             200             205

Glu Ile Leu Ile Phe Lys Asp Arg His Phe Trp Arg Lys Ser Leu Arg
             210             215             220

Lys Leu Glu Pro Glu Leu His Leu Ile Ser Ser Phe Trp Pro Ser Leu
             225             230             235

Pro Ser Gly Val Asp Ala Ala Tyr Glu Val Thr Ser Lys Asp Leu Val
             240             245             250

Phe Ile Phe Lys Gly Asn Gln Phe Trp Ala Ile Arg Gly Asn Glu Val
         255             260             265

Arg Ala Gly Tyr Pro Arg Gly Ile His Thr Leu Gly Phe Pro Pro Thr
270             275             280             285

Val Arg Lys Ile Asp Ala Ala Ile Ser Asp Lys Glu Lys Asn Lys Thr
             290             295             300

Tyr Phe Phe Val Glu Asp Lys Tyr Trp Arg Phe Asp Glu Lys Arg Asn
             305             310             315

Ser Met Glu Pro Gly Phe Pro Lys Gln Ile Ala Glu Asp Phe Pro Gly
         320             325             330

Ile Asp Ser Lys Ile Asp Ala Val Phe Glu Glu Phe Gly Phe Phe Tyr
335             340             345

Phe Phe Thr Gly Ser Ser Gln Leu Glu Phe Asp Pro Asn Ala Lys Lys
350             355             360             365

Val Thr His Thr Leu Lys Ser Asn Ser Trp Leu Asn Cys
             370             375
```

(2) INFORMATION FOR SEQ ID NO:2:

(i) SEQUENCE CHARACTERISTICS:
        (A) LENGTH: 173 amino acids (B) TYPE: amino acid
                    (C) STRANDEDNESS: single
                    (D) TOPOLOGY: linear (ii) MOLECULE TYPE: peptide (xi) SEQUENCE DESCRIPTION: SEQ ID NO:2:

Tyr Ser Leu Phe Pro Asn Ser Pro Lys Trp Thr Ser Lys Val Val Thr
1               5                  10                  15

Tyr Arg Ile Val Ser Tyr Thr Arg Asp Leu Pro His Ile Thr Val Asp
            20                  25                  30

Arg Leu Val Ser Lys Ala Leu Asn Met Trp Gly Lys Glu Ile Pro Leu
        35                  40                  45

His Phe Arg Lys Val Val Trp Gly Thr Ala Asp Ile Met Ile Gly Phe
    50                  55                  60

Ala Arg Gly Ala His Gly Asp Ser Tyr Pro Phe Asp Gly Pro Gly Asn
65                  70                  75                  80

Thr Leu Ala His Ala Phe Ala Pro Gly Thr Gly Leu Gly Gly Asp Ala
                85                  90                  95

His Phe Asp Glu Asp Glu Arg Trp Thr Asp Gly Ser Ser Leu Gly Ile
            100                 105                 110

Asn Phe Leu Tyr Ala Ala Thr His Glu Leu Gly His Ser Leu Gly Met
        115                 120                 125

Gly His Ser Ser Asp Pro Asn Ala Val Met Tyr Pro Thr Tyr Gly Asn
    130                 135                 140

Gly Asp Pro Gln Asn Phe Lys Leu Ser Gln Asp Asp Ile Lys Gly Ile
145                 150                 155                 160

Gln Lys Leu Tyr Gly Lys Arg Ser Asn Ser Arg Lys Lys
                165                 170

(2) INFORMATION FOR SEQ ID NO:3:

(i) SEQUENCE CHARACTERISTICS:
            (A) LENGTH: 31 base pairs
            (B) TYPE: nucleic acid
            (C) STRANDEDNESS: double
            (D) TOPOLOGY: circular (ii) MOLECULE TYPE: DNA (genomic)

(ix) FEATURE:
            (A) NAME/KEY: CDS
            (B) LOCATION: 17..31

(xi) SEQUENCE DESCRIPTION: SEQ ID NO:3:

AGAAGGAGAT ATACAT ATG GCT AGC TTC AGA                                31
                  Met Ala Ser Phe Arg
                   1               5

(2) INFORMATION FOR SEQ ID NO:4:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (xi) SEQUENCE DESCRIPTION: SEQ ID NO:4:

Met Ala Ser Phe Arg
1               5

(2) INFORMATION FOR SEQ ID NO:5:

```
        (i) SEQUENCE CHARACTERISTICS:
            (A) LENGTH: 37 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:5:

Phe Arg Thr Phe Pro Gly Ile Pro Lys Trp Arg Lys Thr His Leu Thr
1               5                  10                  15

Tyr Arg Ile Val Asn Tyr Thr Pro Asp Leu Pro Lys Asp Ala Val Asp
                20                  25                  30

Ser Ala Val Glu Lys
            35

(2) INFORMATION FOR SEQ ID NO:6:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:6:

GGATCACCAG CTAGCTATCC ATTGGATGGA GCTGCA                            36

(2) INFORMATION FOR SEQ ID NO:7:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:7:

GCACTCGAAT TCTGCAGTCA GGGGGTCTCA GGGGAGTCAG                        40

(2) INFORMATION FOR SEQ ID NO:8:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Thiolester-bond
            (B) LOCATION: 3..4

(xi) SEQUENCE DESCRIPTION: SEQ ID NO:8:

Pro Leu Gly Leu Leu Gly
1               5
```